United States Patent [19]

Walston

[11] Patent Number: 5,063,939
[45] Date of Patent: Nov. 12, 1991

[54] MALE CONTRACEPTIVE DEVICE

[76] Inventor: Wayne T. Walston, 505 S. 24th St., Arlington, Va. 22202

[21] Appl. No.: 577,747

[22] Filed: Sep. 5, 1990

[51] Int. Cl.$^5$ .............................................. A61F 6/02
[52] U.S. Cl. .................... 128/842; 128/82.1; 128/402
[58] Field of Search ................ 604/55; 128/842, 82.1, 128/157, 891, 82, 402

[56] References Cited

U.S. PATENT DOCUMENTS

| | | | |
|---|---|---|---|
| 14,085 | 1/1856 | Cheever . | |
| 847,779 | 3/1907 | Jarrett | 128/158 |
| 850,298 | 4/1907 | DeMars | 128/157 |
| 1,399,095 | 12/1921 | Webb | 128/402 |
| 2,298,298 | 10/1941 | Joy | 128/402 |
| 2,867,215 | 1/1959 | Horton | 128/82.1 |
| 3,292,628 | 12/1966 | Maxwell | 128/402 |
| 3,518,995 | 10/1967 | Claff et al. . | |
| 3,901,224 | 8/1975 | Bucalo | 128/842 |
| 4,073,289 | 2/1978 | Fahim | 128/842 |
| 4,404,460 | 9/1985 | Kerr | 128/402 |
| 4,413,624 | 11/1983 | Snow | 128/399 |
| 4,705,935 | 11/1989 | Traffanstedt et al. | 219/211 |

FOREIGN PATENT DOCUMENTS

| | | | |
|---|---|---|---|
| 436224 | 3/1912 | France | 128/38 |
| 591747 | 4/1925 | France | 128/402 |

Primary Examiner—Robert A. Hafer
Assistant Examiner—David Kenealy
Attorney, Agent, or Firm—Evenson, Wands, Edwards, Lenahan & McKeown

[57] ABSTRACT

A male contraceptive device includes a resistive heating unit secured in an insulated scrotum sack. The heating unit is linked to a control unit by conductors. The control unit forms part of a carrying case worn at the user's waistline and which contains a power source, on-off switch, low battery indicator, defective element indicator, timer, beeper and telethermometer. The control unit and heating unit produce a significant increase in intrascrotal temperature which creates a suppression of spermatogenesis rendering the person temporarily sterile. The heating unit can be concentrated at the posterior end of the sack for quickly suppressing spermatogenesis in the human epididymis.

16 Claims, 7 Drawing Sheets

MALE CONTRACEPTIVE DEVICE

BACKGROUND AND SUMMARY OF THE INVENTION

This invention relates to the field of contraceptive devices and, more particularly, to a birth control device designed to limit sperm production by effecting a temperature increase in the male testes.

It is known that the male scrotum regulates testicular temperature and that an increase in scrotal temperature causes a suppression of spermatogenesis. Clinical findings of these affects are documented in "Effect of Induced Intrascrotal Hyperthermia on Testicular Function in Man", *American Journal of Obstetrics and Gynecology*, John Rock, M.D. and Derek Robinson, M.D., Volume 93, No. 6, Nov. 15, 1965 and "Intrascrotal Hyperthermia Induced by Scrotal Insulation: Affect on Spermatogenesis", *Obstetrics and Gynecology*, Volume 29, No. 2, February 1967.

As a result of these findings, attempts have been made to provide a device which increases scrotal temperature and is acceptable to a large number of men. These devices have taken the form of scrotum insulators which are designed to be worn by the man for several hours each day. Insulating materials are used in an article of clothing worn by the man which covers and holds the scrotum against the body of the person in a manner to exclude free circulation of air about the scrotum.

The prior known scrotum insulators must be worn over 14 hours each day in order to affect the necessary increase in scrotum temperature to drop the spermatozoa count to a level considered infertile. Scrotum insulators of this type are known from U.S. Pat. Nos. 3,518,995 and 4,413,624.

As noted above, these prior scrotum insulators must be worn for extended periods of time in order to be effective. This extended use is often burdensome and uncomfortable for the male user. There is therefore needed a male contraceptive device which increases scrotal temperature to render the user oligospermatic and thus infertile and which requires minimal use each day and achieves sterilization in a short time period. The device should further be comfortable to wear.

The present invention meets these needs by providing a male contraceptive device including a scrotum sack having coupled thereto an electrical heating unit to precisely and controllably increase the intrascrotal temperature. The present invention has the advantage of requiring only minimal daily use in the order of 30 minutes to 2 hours to render a man sterile within a short time period such as 3-7 weeks. Further, by wearing the device for longer periods each day, the user's sperm count can drop to a level considered as sterile in a very short time period.

The present invention has the advantages of allowing sexual activity to occur without interruption. Further, physical and emotional side affects associated with other contraceptive methods are avoided. Also, suppression of spermatogenesis is reversible in that discontinuing use of the device eventually causes the man's sperm count to return to its normal level after a brief rise above the normal level. The device of the present invention further has the advantage of not requiring any chemical methods or techniques which interfere with the act of sex.

It is a further advantage of the present invention to provide a contraceptive device which is 100% natural and takes advantage of the natural accessibility of the production of sperm cells in the male testes. In the early stages of the human development, the testes are located inside the abdomen. They later descend into the scrotum outside of the male body, since fertile sperm will not mature properly at normal body temperatures. Each testes is packed with coil-like tubes. The tubes are lined with cells which multiply and develop still further cells. At the mature state of the sperm cells, tails are formed which propel the sperm through the cervix and into the uterus. Spermatic ducts connect the testes to the penis. These ducts loop back into the abdomen and curve around the bladder to enter the penis through the urethra. The sperm are suspended in a seminal fluid just prior to ejaculation. The seminal fluid is manufactured by several glands located at the base of the bladder, the largest gland being the prostrate gland.

Because sperm cells die when at a temperature a few degrees above their controlled environment, the present invention creates an artificial environment from a scrotum sack and electrical heating means to raise the temperature beyond that at which the sperm can survive. This eliminates the possibility of spermatogenesis until the renewal of the next generation of sperm cells. In order to continue infertile, the heating process is again applied to suppress spermatogenesis to the next generation of sperm cells.

It is a further advantage of the invention to provide an electrical heating unit including an electrical control device which may be worn at the user's waist, e.g. like a message beeper. This control device may be battery operated and includes a timer, automatic shutoff switch, low-battery signal indicator, and a warning indicator for any defective elements. The use of the control device allows precise regulation of the scrotum temperature and hours of use. This allows for a more accurate determination of when the user desires to reach an infertile state.

It is yet a further advantage of the present invention to arrange a large number of the heating elements for the scrotum sack at the posterior side of the sack. This allows an increased heat concentration near the human epididymis which is the final and crucial stage of development for the sperm cells, i.e., the stage at which sperm develop their tails necessary for mobility to travel to the ovum for conception.

It is still a further advantage to provide for individually-controllable heating elements associated with each testes. This allows for maximum controllability of the heat distribution.

Other objects, advantages and novel features of the present invention will become apparent from the following detailed description of the invention when considered in conjunction with the accompanying drawings.

DETAILED DESCRIPTION OF THE DRAWINGS

Figure 1:
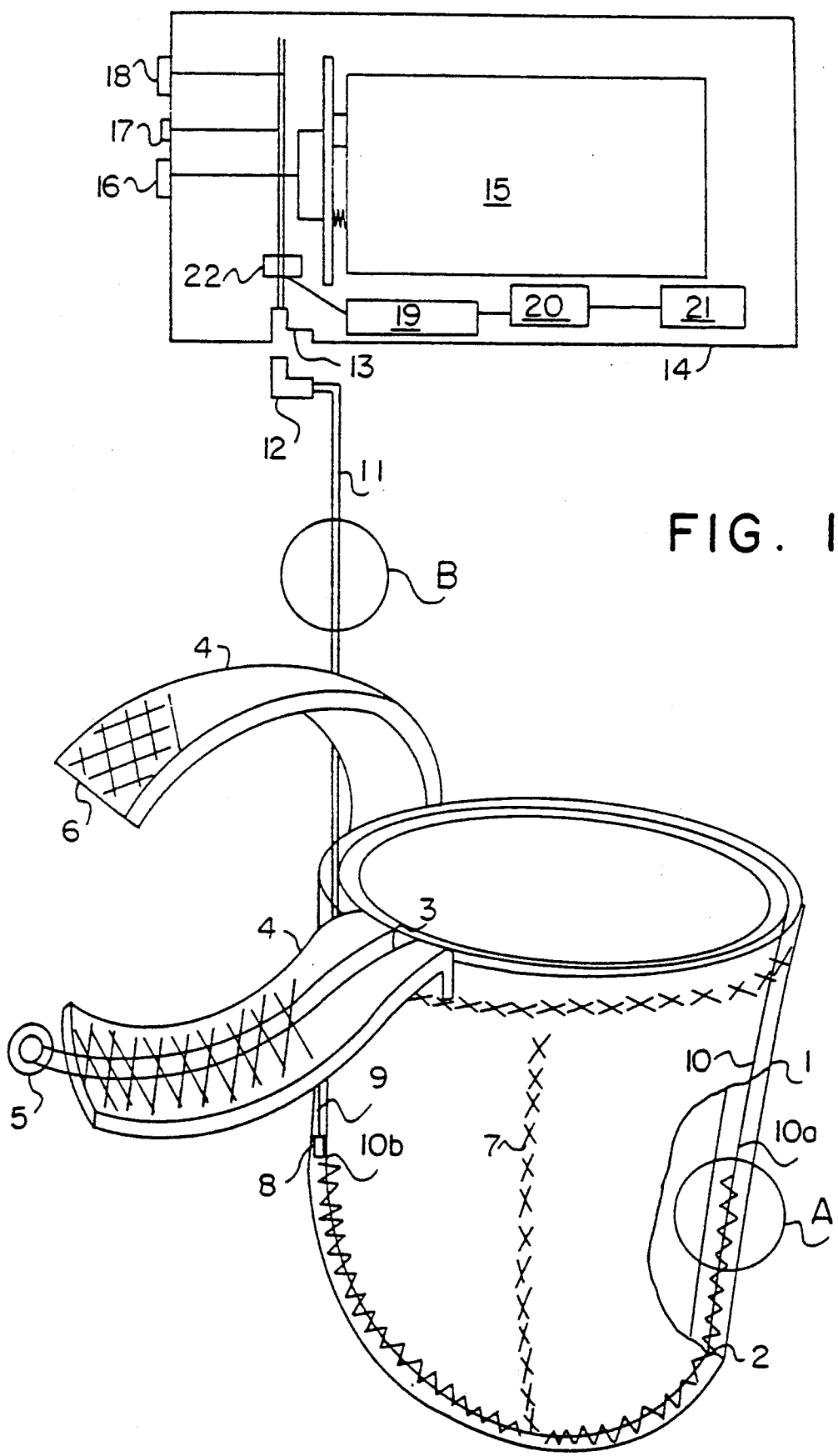
FIG. 1 is a schematic illustration of the male contraceptive device of the present invention.

Referring to FIG. 1, there is shown a male contraceptive device including a scrotum sack generally designated 1 and an electrical control unit 14. The sack 1 is designed to encircle the male scrotum. The sack 1 can have any form, such as jockey straps traditionally worn by athletes or other designs which allow encircling of the scrotum and/or the penis to hold and maintain the heat generated according to the invention.

The sack 1 is shown stitched together by traditional methods of sewing, indicated generally at 7. Fastening straps 4 are attached to the open portion of the sack 1 and can be fastened around the male penis to form a snug fit. The fastening straps 4 can be formed in two sections made of a cloth material to prevent the sack 1 from falling off of the scrotum. A pull string 3, made of any suitable material, is sewn in the upper circumference of the sack 1 and extends through one of the straps 4. The string 3 extends out of the strap 4 and terminates as a pull string lock 5. The pull string lock 5 operates to lock when an appropriate tightness has been achieved around the scrotum. The pull string lock 5 can be of any suitable design such as those used on military backpacks.

Located between layers of the sack 1 is a thermistor 8 which registers temperature within the sack 1. The thermistor 8 is coupled via conducting wire 9 to the electrical control unit box 14. A further conducting wire 10 is shown on the interior portion of the sack 1. This wire 10 includes resistive heating units 2 for heating the scrotum sack 1. The resistive heating units 2 are coupled at one end to a positive line 10a and at the other end to a negative line 10b. The conducting wires 9 and 10 are housed in a main insulating conductor housing 11 outside of the sack 1. The insulating conductor housing 11 includes a male connector socket 12 located at the end opposite that of the sack 1.

The electrical control unit 14 may be of the carrying case type as shown in FIG. 1 with the front of the case removed. The carrying case 14 may be made of any durable, light-weight material. Preferably, a high-impact plastic similar to that used in message beepers is used for the carrying case 14. The carrying case 14 is designed to be worn around the user's waistline.

Inside the case 14, a battery 15 is shown for generating electricity through the conducting wires 9 and 10 to the resistive heating units 2 located in the sack 1. A female connector socket 13 located in the carrying case 14 receives the male connector plug 12 to electrically couple the sack 1 with the electric control unit 14. A rheostat 22, telethermometer 19, timer 20 and beeper 21 are coupled together to form a control circuit with the battery source 15. An on-off switch 16, low battery warning light 17, and a defective element indicator 18 are located on the outside of the carrying case 14 and are coupled to the control circuit.

In operation, the on-off switch 16 is set to its on position. The switch 16 has appropriate time slots preferably representing every half-hour and having a total period of two hours. Once the switch 16 is turned on, the timer 20 is alerted that telethermometer 19 should register an appropriate temperature within a prescribed time interval, e.g. 15 minutes, or otherwise the element warning light 18 will light indicating that the resistive heating units 2 have failed to function properly to create the desired temperature within the scrotum sack 1.

If there is no malfunction, then once the appropriate temperature is reached in the scrotum sack 1, as indicated by telethermometer 19, then the rheostat 22 functions to regulate the strength of the current provided to the scrotum sack 1. The appropriate temperature should be in the range of 39°–44° C. The timer 20 functions to time the heating procedure and activates the beeper 21 which sounds to indicate the end of the scrotum heating process.

Figure 2:
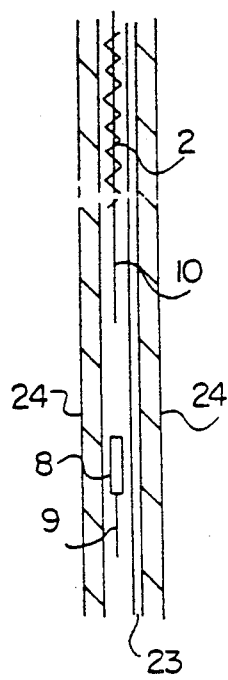
FIG. 2 is a cross-section view along lines II—II in FIG. 3.

FIG. 2 is a cross-section view of the sack 1 as indicated generally at A in FIG. 1. The sack 1 is formed having inner and outer layers 24 between which a middle layer 23 is formed. The layers 24 may be of a cotton flannel material and the layer 23 may be formed of Milium material. The Milium layer 23 is a fabric having an aluminum coating of such thinness that it retains its flexibility and still maintains a high heat reflective ability. Between the Milium layer 23 and inner layer 24, the resistive heating unit 2, thermistor 8 and conducting wires 9 and 10 are located. The cotton flannel layers 24 provide comfort for the wearer of the device.

Figure 3:
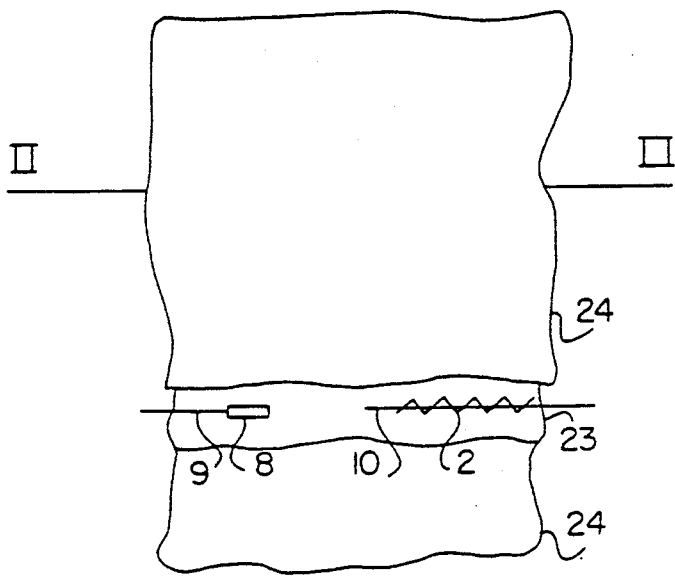
FIG. 3 is an illustration of a portion of the material used in forming the scrotum sack of FIG. 1.

FIG. 3 is a view of a portion of the scrotum sack 1 from the inside having a cut-away section. As the heat is generated by the resistive heating unit 2, the Milium fabric 23 functions as the main heat reflective shield in helping the temperatures reach the desired levels, e.g. 39°–44° C., in a relatively short time period.

Figure 4:
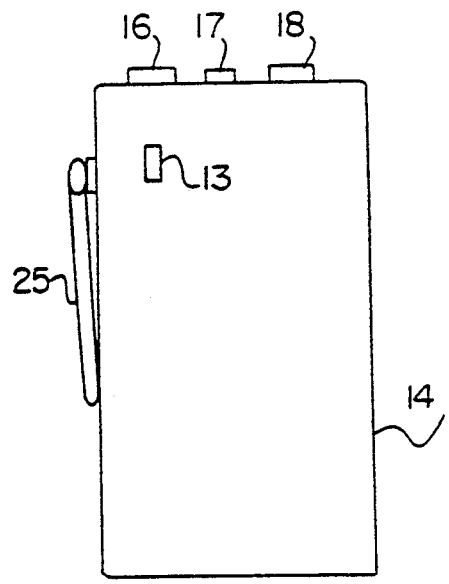
FIG. 4 is a side view of the carrying case shown in FIG. 1.
Figure 5:
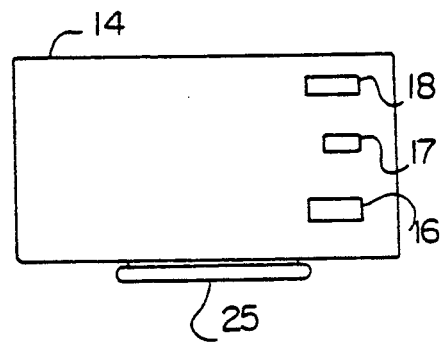
FIG. 5 is a top view of the carrying case shown in FIG. 1.

Referring to FIGS. 4 and 5, there are shown side and top views of the carrying case 14, respectively. The carrying case 14 includes a clip 25 to allow the case 14 to be worn around the user's waistline, e.g. clipped on to the user's pants or belt. The female connector socket 13 is shown which couples to the main conductor housing 11 through the male connector socket 12. The on-off switch 16, low battery indicator 17 and malfunction indicator 18 can be of any conventional type well known to those skilled in the art. The low battery indicator light 17 warns the user that the battery's energy is too low to generate the appropriate amount of current to heat the sack 1.

Figure 6:
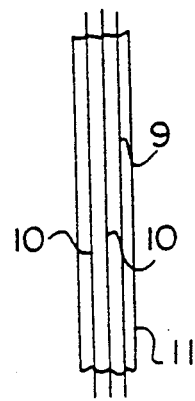
FIG. 6 is an enlargement of area B denoted in FIG. 1.

FIG. 6 is an enlargement of area B in FIG. 1 showing the main conductor housing 11, including conducting wires 9 and 10. The housing 11 can be of any insulating material such as that used in conventional electrical wiring.

Figure 7A:
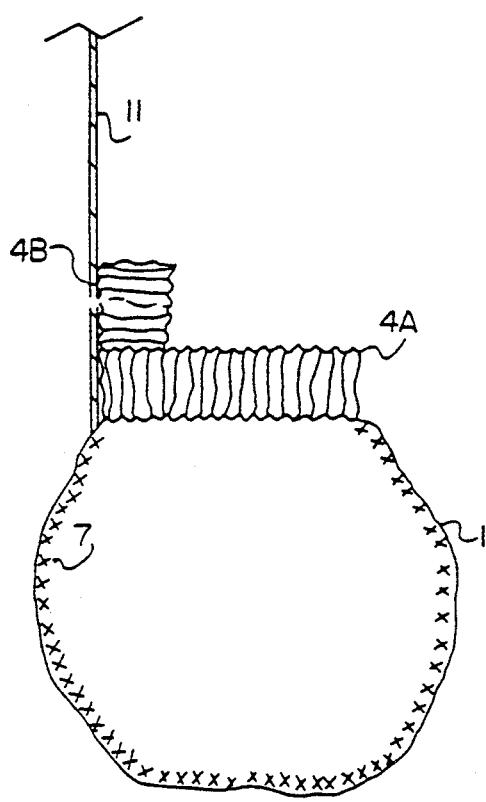
FIGS. 7a and 7b are side and frontal views, respectively, of an embodiment of the scrotum sack of the present invention.
Figure 7B:
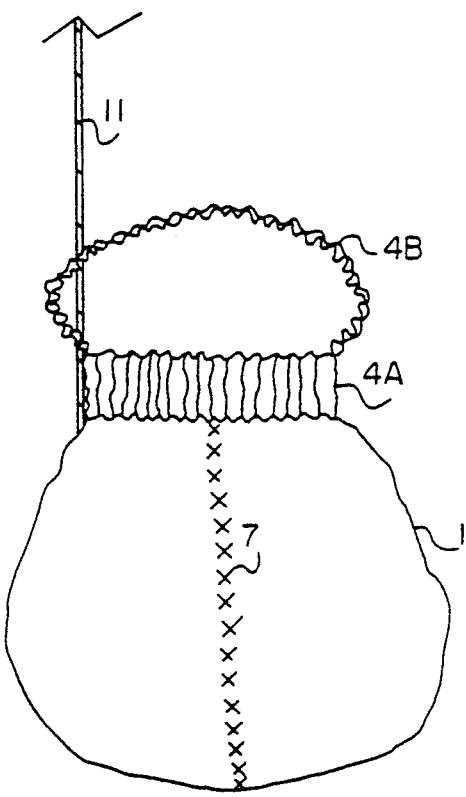

Referring to FIGS. 7a and 7b, there are shown side and frontal views of an embodiment of the scrotum sack 1 shown in FIG. 1. Around the circumference of the open end of the scrotum sack 1, a continuous elastic stretch band 4a is provided in lieu of the pull string 3. The stretch band 4a includes an extension portion 4b which encircles the penis at its posterior section. The elastic extension 4b is designed to stretch to allow the penis to fit through the loop formed therein. Further, the elastic band 4a stretches open to allow the scrotum to fit within the insulated scrotum sack 1.

Figure 8:
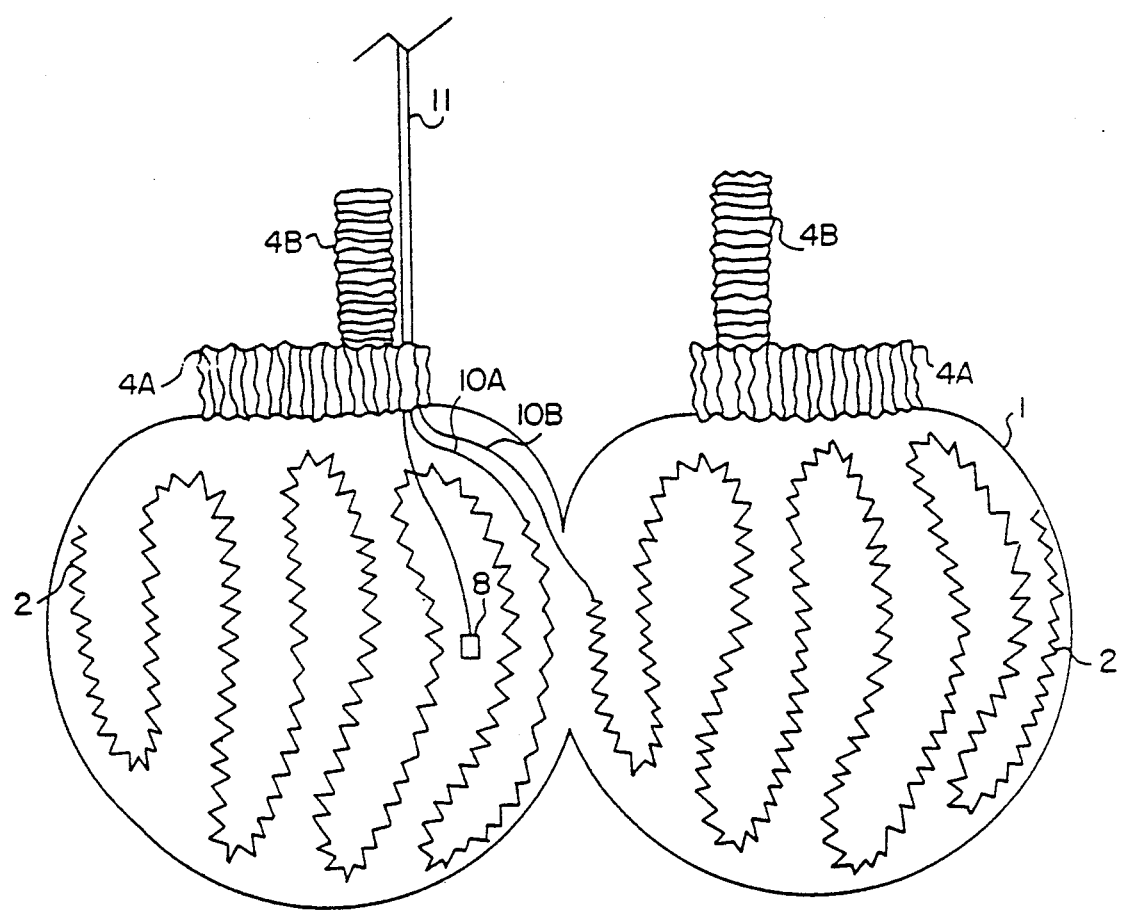
FIG. 8 is an illustrative sagittal section view of the embodiment of FIGS. 7a and 7b.

FIG. 8 is a sagittal section view of the device in FIG. 7 showing the arrangement of the resistive heating units 2 within the sack 1. The resistive heating units 2 provide continuous coverage over the sack exterior to allow for complete encirclement of the scrotum. This provides efficient distribution of the heat in the sack 1.

Figure 9:
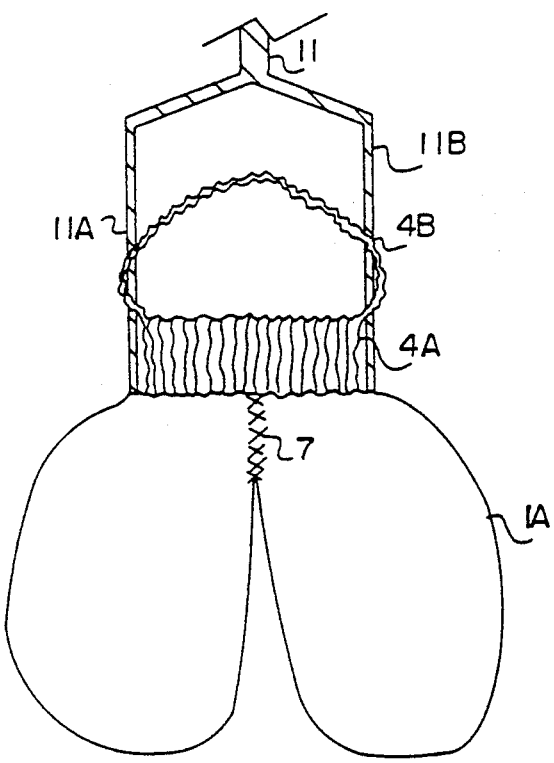
FIG. 9 is an illustrative frontal view of another embodiment of the present invention.

Referring to FIG. 9, there is shown a front view of another embodiment for the scrotum sack 1 designated here as 1a. In this embodiment, the scrotum sack 1a is formed from two individual compartmental sacks, one compartment for each testicle. The use of two sacks provides maximum heat control wherein each testes itself is individually encircled by resistive heating units 2a as shown in the double-sagittal sectional view of FIG. 9a. The resistive heating elements 2a are concentrated in the posterior of the scrotum sack 1a. This higher concentration of resistive heating units is provided at the position of the human epididymis which lies upon the outer edge of the posterior border of the testes and the vas deferens. The vas deferens is the continuation of the epididymis. As shown in FIG. 10, beginning at the lower part of the globus minor, the vas deferens ascends along the posterior border of the testes and along the inner side of the epididymis. Because the epididymis is the final stage of development for the sperm, being the place where the sperm are stored and develop their ability to swim and fertilize eggs, the higher concentration of resistive heating elements 2a near the epididymis provides a fast and efficient device for lowering the sperm count.

Figure 9A:
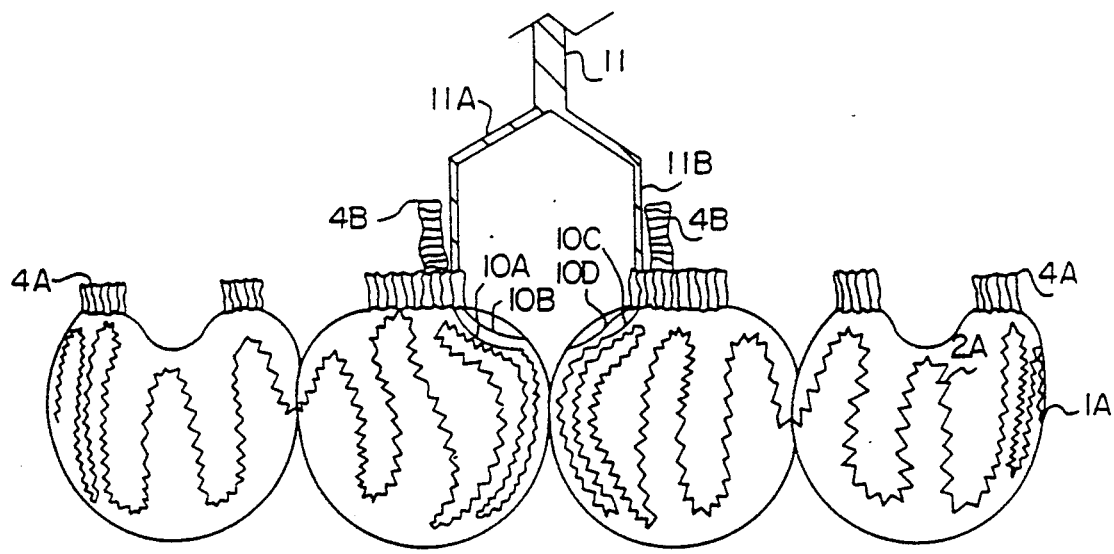
FIG. 9a is a double-sagittal sectional view of the scrotum sack shown in FIG. 9.
Figure 10:
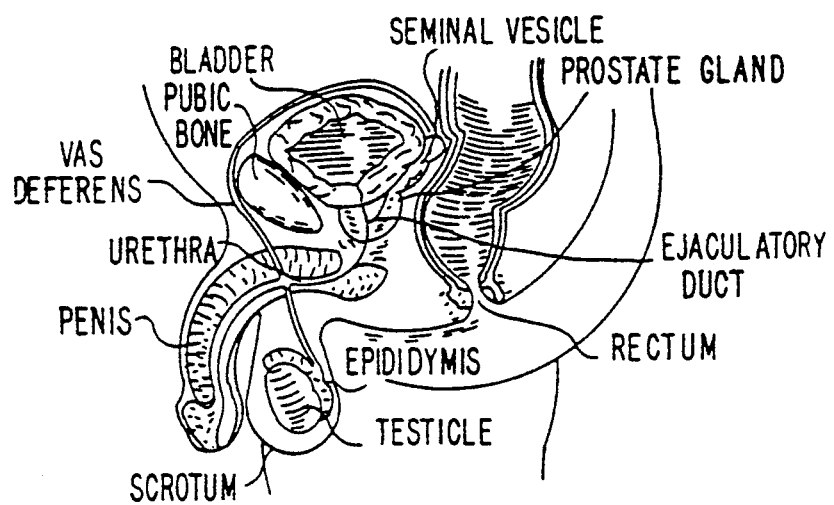
FIG. 10 is a side view of the male reproductive organs.

As shown in FIGS. 9 and 9a, each individual sack 1a has an independent heating element 2a. The heating elements 2a are coupled via conducting cords 11a and 11b leading to the main conducting cord 11. Conducting wires 10a and 10b for one sack and conducting wires 10c and 10d for the other sack are all provided in the insulated housing conducting cord 11 to the electrical control unit 14.

In operation of the male contraceptive device, the battery 15 generates electrical current which passes through the conducting wires to the resistive heating units. The resistive heating units create the heat necessary to raise the temperature in the scrotum sack, thus causing intra-scrotal hypothermia to result. The control unit includes a beeper to indicate to the wearer that the scrotum heating process has ended, as controlled by the timer.

The scrotum heating device is designed to raise the temperature within the scrotum to 39°-44° C. The device regulates this temperature raise between approximately 30 minutes to two hours each day to render a man sterile for all practical purposes within three to seven weeks. Infertility can be verified by taking a sample of the user's sperm to a fertility specialist to confirm the sperm count has fallen below a 20 mil per cc level. With a sperm count below this level, the individual is effectively sterile.

It is to be understood that the invention can be operated for other time limits or temperature ranges as are appropriate and medically safe to achieve the desired infertility. Further, the design of the insulating scrotum sack is not limited to those described herein nor is the basic design of the energy source mechanism for generating the energy limited to those described herein. As many variations as could be made to the above without departing from the scope of the invention are contemplated.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A contraception device for a human male, comprising:
   a flexible sack for receiving a scrotum;
   resistive heating elements for heating the scrotum formed as part of said flexible sack;
   means for controlling said resistive heating elements such that the scrotum is heated to a predetermined temperature range for a predetermined time period in order to suppress spermatogenesis in the scrotum to render the human male sterile;
   said control means including:
      a control switch for turning on the device and coupling current to said resistive heating elements;
      a thermistor arranged within said flexible sack for registering temperatures within the sack;
      a rheostat coupled to said resistive heating elements for regulating the current; and
      a telethermometer coupled to the thermistor for indicating when the predetermined temperature range is reached such that said rheostat can regulate the strength of the current to the resistive heating elements.

2. A contraceptive device for a human male, comprising:
   a flexible sack, having a posterior end, for receiving a scrotum;
   resistive heating elements for heating the scrotum formed as part of said flexible sack, said resistive heating elements being concentrated in the posterior end of the sack; and
   means for controlling said resistive heating elements such that the scrotum is heated to a predetermined temperature range for a predetermined time period in order to suppress spermatogenesis in the scrotum.

3. A male contraceptive device according to claim 1, wherein the flexible sack comprises:
   a layered construction including an outer layer formed of a soft cloth material;
   an inner layer formed of a soft cloth material;
   an intermediate layer against the outer layer formed of a thin, heat reflective material; and
   wherein the resistive heating elements are arranged between the intermediate and inner layers of the sack to heat the scrotum.

4. A male contraceptive device according to claim 3, further comprising:
   a fastening strap having first and second portions, said portions being coupled at their one end to the sack, the strap fastening around a penis to hold the sack on the scrotum;
   a pull string sewn within the sack and extending around the circumference of the sack opening, the pull string further extending through one of said strap portions; and
   a pull string lock coupled to the end of the pull string extending from the one strap portion, the pull string and pull string lock being used to snugly fit and tighten the sack around the scrotum.

5. A male contraceptive device according to claim 3, further comprising:
   a first elastic stretch band coupled at each end to the sack;
   wherein the sack further includes a second elastic stretch band formed around the circumference of the sack opening, the first band being used to encircle the penis to hold the sack on the scrotum and the second band allowing the sack to stretch open to receive the scrotum.

6. A male contraceptive device according to claim 1, wherein the control means further includes:
   a timer for timing the heating operation of the device;
   a beeper coupled to the timer for indicating the end of the heating operation;
   a low power indicator; and
   a malfunction indicator for indicating whether the heater is operating properly.

7. A male contraceptive device according to claim 6, wherein the control means is housed in a high-impact plastic case, said control switch, low power indicator and malfunction indicator being visible from outside said case.

8. A male contraceptive device according to claim 3, wherein the flexible sack includes:
   first and second sacks individually compartmented, each sack receiving one testes of the scrotum; and
   wherein the means for resistive heating are concentrated at the posterior end of the first and second sack.

9. A male contraceptive device according to claim 8, wherein the means for resistive heating located in each sack are individually controllable by the control unit.

10. A male contraceptive device according to claim 3, wherein the outer and inner layers are made of a cotton-flannel material; and
    wherein the intermediate layer is made of an alumized cloth material.

11. A male contraceptive device according to claim 2, wherein the control means includes:
    a control switch for turning on the device;
    a thermistor formed as part of the sack to register temperatures within the sack;
    a rheostat coupled with the electrical heater, the rheostat regulating the current to the heater; and
    a telethermometer coupled with the thermistor for indicating when the proper sack temperature is reached.

12. A male contraceptive device according to claim 11, wherein the control means further includes:
    a timer for timing the heating operation of the device;
    a beeper coupled to the timer for indicating the end of the heating operation;
    a low power indicator; and
    a malfunction indicator for indicating whether the heater is operating properly.

13. A male contraceptive device according to claim 12, wherein the control means is housed in a high-impact plastic case, said control switch, low power indicator and malfunction indicator being visible from outside said case.

14. A birth control method for a human male, the method comprising the steps of:
    (a) attaching an insulated scrotum sack having an electrical heater around a male scrotum;
    (b) electrically heating the sack and scrotum into a temperature range of approximately 39°–44° C.;
    (c) timing the duration of the electrically heating step with a timer;
    (d) discontinuing the use of the scrotum sack once the timer reaches a predetermined time for minimizing the daily use of the scrotum sack in achieving infertility within a short time period;
    (e) repeating steps (a), (b), (c), and (d) each day until the human male is sterile.

15. A birth control method according to claim 14, further comprising the step of intermittently testing the human male to determine a sperm count of the human male.

16. A birth control method according to claim 15, wherein said step of repeating steps (a), (b), (c), and (d) is carried out until the sperm count is below a 20 mill per cc level wherein the human male is effectively sterile.

* * * * *